(12) United States Patent
Shener et al.

(10) Patent No.: US 9,572,921 B2
(45) Date of Patent: Feb. 21, 2017

(54) CARTRIDGE ASSEMBLY

(75) Inventors: Cemal Shener, Woburn, MA (US);
Brian Loreth, Braintree, MA (US);
Petter Hedstrom, Haverhill, MA (US);
Guy Checketts, York (GB)

(73) Assignee: Smith & Nephew, Inc., Austin, TX (US)

( * ) Notice: Subject to any disclaimer, the term of this patent is extended or adjusted under 35 U.S.C. 154(b) by 277 days.

(21) Appl. No.: 12/353,331

(22) Filed: Jan. 14, 2009

(65) Prior Publication Data

US 2010/0152647 A1    Jun. 17, 2010

Related U.S. Application Data

(60) Provisional application No. 61/138,395, filed on Dec. 17, 2008.

(51) Int. Cl.
*A61M 3/02* (2006.01)

(52) U.S. Cl.
CPC ........ *A61M 3/0258* (2013.01); *A61M 2205/12* (2013.01); *A61M 2205/60* (2013.01); *Y10T 137/598* (2015.04); *Y10T 137/8593* (2015.04)

(58) Field of Classification Search
CPC .................. B65D 85/8043; A61M 2001/1645; A61M 2205/14; A61M 1/28; A61M 2001/3656; A61M 1/1694; A61M 2205/12; A61M 3/0258; A61M 2205/60; A61M 2005/3142; Y10T 137/598; Y10T 137/8593
USPC ... 604/27, 30, 131, 118, 119, 120, 121, 123, 604/153
See application file for complete search history.

(56) References Cited

U.S. PATENT DOCUMENTS

| | | | |
|---|---|---|---|
| 3,597,124 A * | 8/1971 | Adams | 417/477.11 |
| 4,769,012 A | 9/1988 | Quang et al. | |
| 4,886,431 A | 12/1989 | Soderquist et al. | |
| 5,403,277 A | 4/1995 | Dodge et al. | |
| 5,460,490 A | 10/1995 | Carr et al. | |
| 5,542,913 A * | 8/1996 | Lindsay | A61M 1/3627 604/4.01 |
| 5,626,563 A * | 5/1997 | Dodge et al. | 604/153 |
| 5,800,383 A | 9/1998 | Chandler et al. | |
| 5,810,766 A * | 9/1998 | Barnitz | A61M 1/0058 604/317 |
| 5,931,808 A | 8/1999 | Pike | |
| 6,322,551 B1 * | 11/2001 | Brugger | 604/533 |
| 2004/0204679 A1 | 10/2004 | Visconti et al. | |
| 2005/0096582 A1 * | 5/2005 | Burnett | 604/9 |
| 2006/0106285 A1 | 5/2006 | Boulais et al. | |
| 2007/0078370 A1 * | 4/2007 | Shener | A61M 3/022 604/8 |

(Continued)

FOREIGN PATENT DOCUMENTS

EP        0533181 A2 *  9/1992  ............. G11B 23/00
JP        H02-299645     11/1990

OTHER PUBLICATIONS

Invitation to pay additional fees and, where applicable, protest fee for PCT/US2009/064692 Dated Jul. 19, 2010.

(Continued)

*Primary Examiner* — Bhisma Mehta
*Assistant Examiner* — Brandy S Lee
(74) *Attorney, Agent, or Firm* — David A. Warmbold

(57) ABSTRACT

The present disclosure relates to a cartridge assembly. The cartridge assembly includes an inflow cartridge and an outflow cartridge removably coupled to the inflow cartridge. An outflow cartridge and a surgical fluid management system are also disclosed.

16 Claims, 13 Drawing Sheets

(56) References Cited

U.S. PATENT DOCUMENTS

| | | |
|---|---|---|
| 2008/0132763 A1 | 6/2008 | Isaacson |
| 2008/0146995 A1 | 6/2008 | Smisson et al. |
| 2008/0154182 A1 | 6/2008 | Martin et al. |
| 2008/0154184 A1* | 6/2008 | Blight ................ A61M 1/0058 604/30 |
| 2008/0154185 A1 | 6/2008 | Blight |
| 2008/0234619 A1 | 9/2008 | Fausset et al. |

OTHER PUBLICATIONS

International search report and written opinion regarding International patent application PCT/US2009/064692 mailed on Jun. 21, 2011.

International Search Report and Written Opinion for PCT/US2009/064692 Dated Oct. 29, 2010.

Office action received in corresponding Chinese application No. 200980157295.0 mailed Apr. 22, 2014.

Office Action issued in corresponding Chinese patent application No. 200980157295.0, mailed Sep. 6, 2013.

Office Action issued in corresponding Japanese patent application No. 2011-542180, mailed Sep. 26, 2013.

Office action received in corresponding Chinese patent application No. 200980157295.0 mailed Oct. 30, 2014.

Foreign office action received in corresponding Australian application No. 2009333745 mailed Oct. 24, 2014.

Office action for corresponding Japanese application No. 2011-542180 mailed Jun. 9, 2014.

EP Office Action dated Jun. 3, 2015, App No. 09760669.3, 6pgs.

Decision of Rejection received in corresponding Chinese patent application No. 200980157295.0 mailed Dec. 4, 2015.

AU Office Action dated Oct. 23, 2015, App No. 2009333745, 3pgs.

Chinese Office Action for app No. 200980157295.0 dated Aug. 18, 2015, 10 pgs.

AU Office Action for app No. 2015249024 dated Jul. 20, 2016, 4 pages.

* cited by examiner

CARTRIDGE ASSEMBLY

CROSS-REFERENCE TO RELATED APPLICATIONS

This application claims priority to U.S. Patent Application No. 61/138,395 filed on Dec. 17, 2008, the disclosure of which is incorporated herein by reference in its entirety.

BACKGROUND

Field of Technology

The present disclosure relates to fluid management for surgical procedures.

Related Art

In an endoscopic procedure, such as arthroscopic surgery, a surgical fluid management system is used to supply fluid to a body cavity. The fluid is delivered to a joint cavity to provide access and visibility to the surgeon performing a surgical procedure within the cavity. The fluid is used to distend the joint, improve viewing of the area being treated, and to remove debris which may be loosened during the procedure.

Current fluid management systems deliver and remove fluid to the treatment site using medical grade tubing. The system must minimally include an inflow tube to provide irrigation fluid to the treatment site and an outflow tube to remove the irrigation from the treatment site. Some systems use completely separate inflow and outflow tubing systems. Other systems use a single cartridge system that includes tubing for both the inflow and the outflow. These single cartridge systems are disposed of after use for each patient.

A fluid management system is needed that utilizes a dual cartridge assembly having one inflow cartridge and one removably coupled outflow cartridge, whereby independent replacement of the outflow cartridge can occur.

SUMMARY OF THE INVENTION

In one aspect, the present disclosure relates to a cartridge assembly. The cartridge assembly includes an inflow cartridge and an outflow cartridge removably coupled to the inflow cartridge. In an embodiment, the outflow cartridge is located laterally to the inflow cartridge. In another embodiment, the outflow cartridge is located proximal to the inflow cartridge. In yet another embodiment, the inflow cartridge includes at least one groove. In a further embodiment, the outflow cartridge includes at least one rail slidably disposed within the at least one groove. In yet a further embodiment, the inflow cartridge includes a latch.

In an embodiment, the outflow cartridge includes a slot, the latch extending into the slot. In another embodiment, the outflow cartridge includes a nose piece, the nose piece including a first tubing connector, a second tubing connector coupled to the first tubing connector, and a third tubing connector. In yet another embodiment, tubing extending from both the first tubing connector and the second tubing connector are coupled to the third tubing connector. In a further embodiment, the inflow cartridge includes a pocket, the outflow cartridge located within the pocket.

In another aspect, the present disclosure relates to an outflow cartridge. The outflow cartridge includes a body and a nose piece coupled to the body, the nose piece including a first tubing connector, a second tubing connector coupled to the first tubing connector, and a third tubing connector, wherein both a first attachment and a second attachment are coupled to an end of the third tubing connector, the first attachment and the second attachment for coupling of tubing extending from the first tubing connector and the second tubing connector to the third tubing connector.

In an embodiment, the outflow cartridge is configured to be removably coupled to an inflow cartridge to form a cartridge assembly. In another embodiment, the outflow cartridge is located laterally to the inflow cartridge. In yet another embodiment, the inflow cartridge includes at least one groove. In a further embodiment, the outflow cartridge includes at least one rail slidably disposed within the at least one groove. In yet a further embodiment, the inflow cartridge includes a latch. In an embodiment, the outflow cartridge includes a slot, the latch extending into the slot.

In yet another aspect, the present disclosure relates to a fluid management system. The fluid management system includes a pump control unit and a cartridge assembly coupled to the pump control unit, the assembly comprising an inflow cartridge and an outflow cartridge removably coupled to the inflow cartridge. In an embodiment, the pump control unit includes a pinch valve. In another embodiment, an extender is coupled to the inflow cartridge, the extender including a first end having a hole and a second end having a hook, the hook running perpendicular to a longitudinal axis of the extender.

In yet another embodiment, the pinch valve is disposed within the hole and the hook is disposed within an opening on the outflow cartridge. In a further embodiment, the outflow cartridge includes a nose piece, the nose piece including a first tubing connector, a second tubing connector coupled to the first tubing connector, and a third tubing connector.

In yet a further embodiment, tubing extending from both the first tubing connector and the second tubing connector are coupled to the third tubing connector, the hook located between the tubing such that movement of the pinch valve engages the pinch valve with either the tubing extending from the first tubing connector or the tubing extending from the second tubing connector. In an embodiment, engagement of the pinch valve with either the tubing extending from the first tubing connector or the tubing extending from the second tubing connector controls fluid flow through the outflow cartridge.

In another embodiment, the pump control unit includes a cartridge recognition switch, the switch disposed within an opening in the inflow cartridge. In yet another embodiment, the inflow cartridge includes an activator, the activator having a first end engaged with the switch and a second end. In yet another embodiment, the outflow cartridge includes a tab, the tab engaged with the second end of the activator. In a further embodiment, engagement of the tab with the second end of the activator provides recognition of connection and removal of the outflow cartridge relative to the inflow cartridge. In yet a further embodiment, the pump control unit includes a magnetic coupling system.

In an embodiment, the inflow cartridge includes a centrifugal pump, the magnetic coupling system and the centrifugal pump acting together to drive fluid through the inflow cartridge. In another embodiment, a vacuum source is coupled to the outflow cartridge. In yet another embodiment, the pump control unit includes a rotor. In a further embodiment, tubing of the outflow cartridge is coupled to the rotor, the rotor acting to drive fluid through the outflow tubing.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION OF THE EMBODIMENTS

The following description of the preferred embodiment(s) is merely exemplary in nature and is in no way intended to limit the disclosure, its application, or uses.

Figure 1:
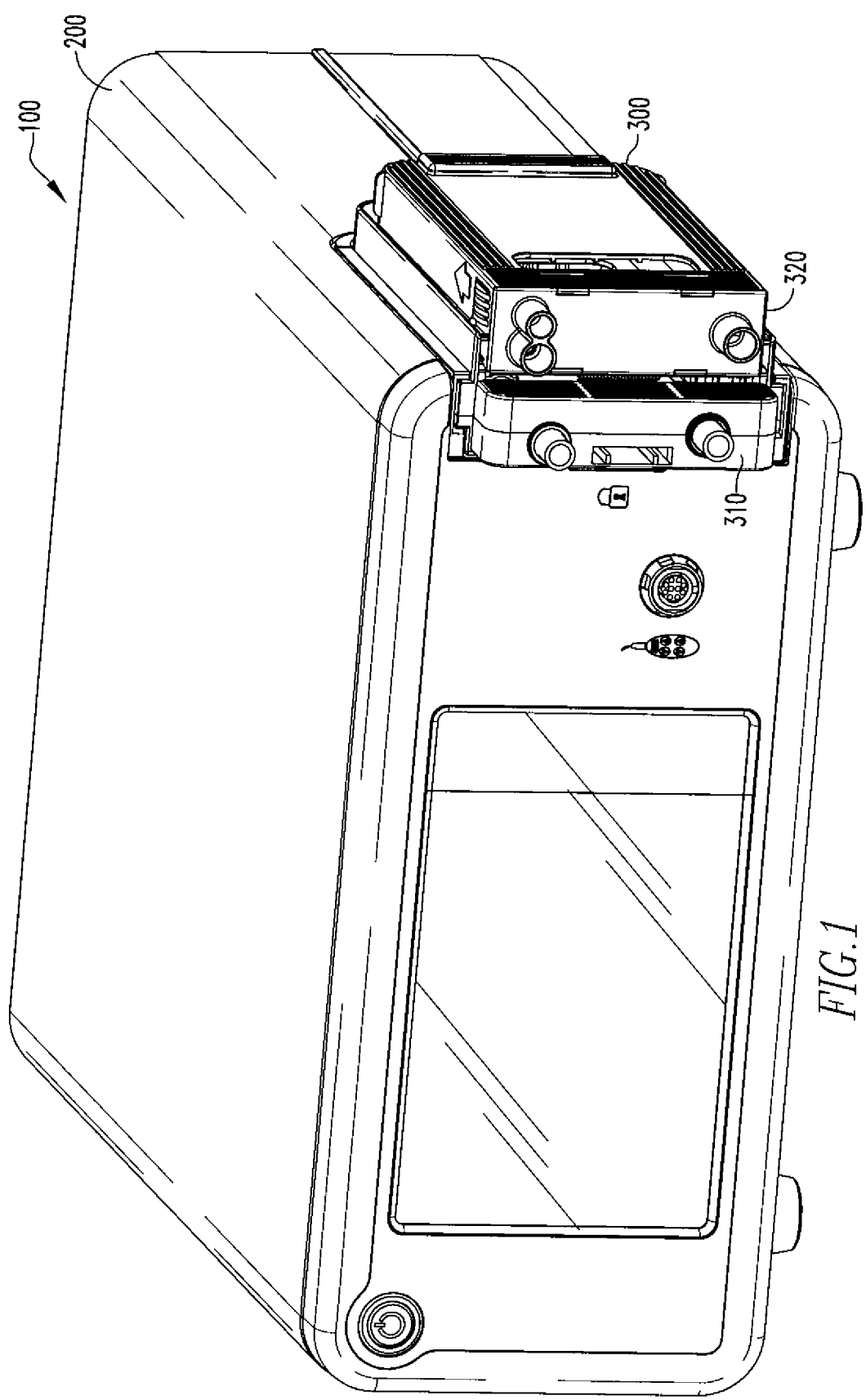
FIG. 1 shows a perspective view of a first embodiment of the fluid management system of the present disclosure.
Figure 2:
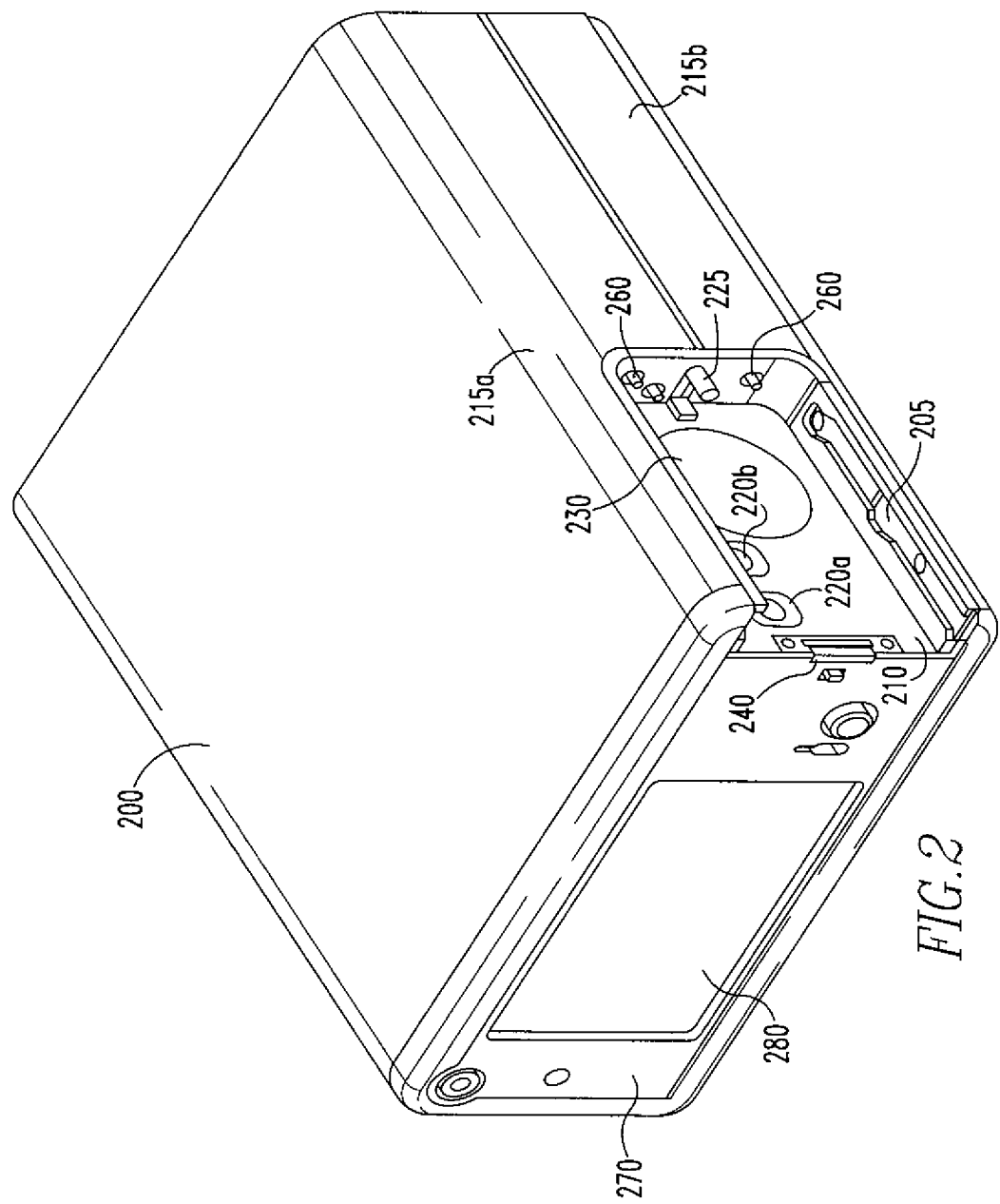
FIG. 2 shows a perspective view of the pump control unit of the fluid management system of FIG. 1.

FIGS. 1 and 2 show a first embodiment of a fluid management system 100 of the present disclosure. The system 100 includes a pump control unit 200 and a cartridge assembly 300. The fluid management system 100 is used in an endoscopic procedure, such as arthroscopic surgery, to supply pressurized fluid to a body cavity. The fluid is delivered to produce a substantially constant predetermined pressure level within the joint cavity. Joint cavity pressure is controlled by the system 100 by varying pump speed, e.g., independent of the rate of flow Q, to maintain a level of joint distension, to provide sufficient access and visibility to the surgeon, and/or to flush the cavity of blood and debris. As the demand for flow rate Q fluctuates throughout a surgical procedure, the system 100 automatically adjusts the control unit 200 to deliver the proper flow rate and to maintain a desired joint pressure in the cavity. The pump control unit 200 and the flow rate are further described in US Patent Application Publication No. US 2007/0078370 ('370 publication), the contents of which are incorporated herein by reference in its entirety.

The pump control unit 200 includes a housing 215a, 215b defining a generally rectangular-shaped slot 210 for operatively receiving cartridge assembly 300, which is removably slid into slot 210. As discussed below, the assembly slot 210 and the cartridge assembly 300 are configured such that the assembly 300 is capable of being inserted into the slot 210 only in a single direction and orientation. The control unit housing 215a, 215b includes an upper section 215a and a lower section 215b removably secured to each other to permit access to an interior of the control unit 200. The assembly 300 includes an inflow cartridge 310 and an outflow cartridge 320 coupled to the inflow cartridge, both of which will be further described below.

The pump control unit 200 includes a front surface 270 having a display 280 providing a graphical user interface. The graphical user interface is, for example, a touch-screen activated interface that permits a user to selectively control or monitor various system parameters. These system parameters are further described in the '370 publication.

Figure 3:
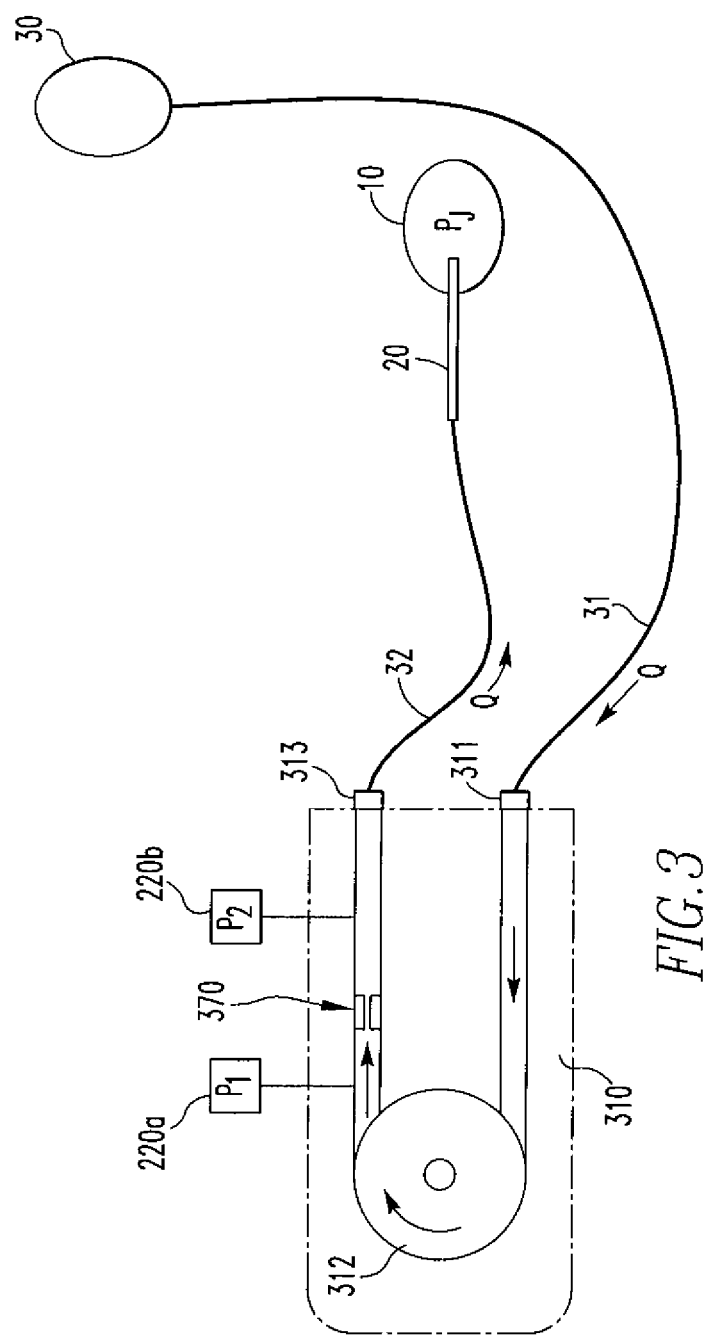
FIG. 3 is a schematic of the fluid management system of FIG. 1 in use during an endoscopic surgical procedure.

Referring to FIGS. 1-3, the pump control unit 200 includes a pair of pressure transducers 220a, 220b for measuring respective pressures P1, P2 across a flow restriction 370 within the cartridge assembly, specifically the inflow cartridge 310, as will be further described below. In use, a fluid bag 30 is operatively connected through medical grade tubing 31 with the inflow cartridge 310 for supplying fluid to a supply fluid inlet tubing connection 311. The inflow cartridge 310 includes a centrifugal pump 312 that cooperates with a magnetic coupling system 230 located within the control unit to supply pressurized fluid at a flow rate Q to joint cavity 10 through an outlet tubing connection 313, a discharge tubing 32, and a cannula 20. The pressure transducers 220a, 220b measure the pressure drop across the flow restriction 370 to derive the flow rate Q. The flow rate Q, along with various system parameters, can be used to generate a transfer function or three-dimensional mathematical model that is used to control flow rate to and fluid pressure within the joint cavity 10, as is further described in the '370 publication. The removal of fluid from the joint cavity 10 via the outflow cartridge 320 will be described below.

Figure 12:
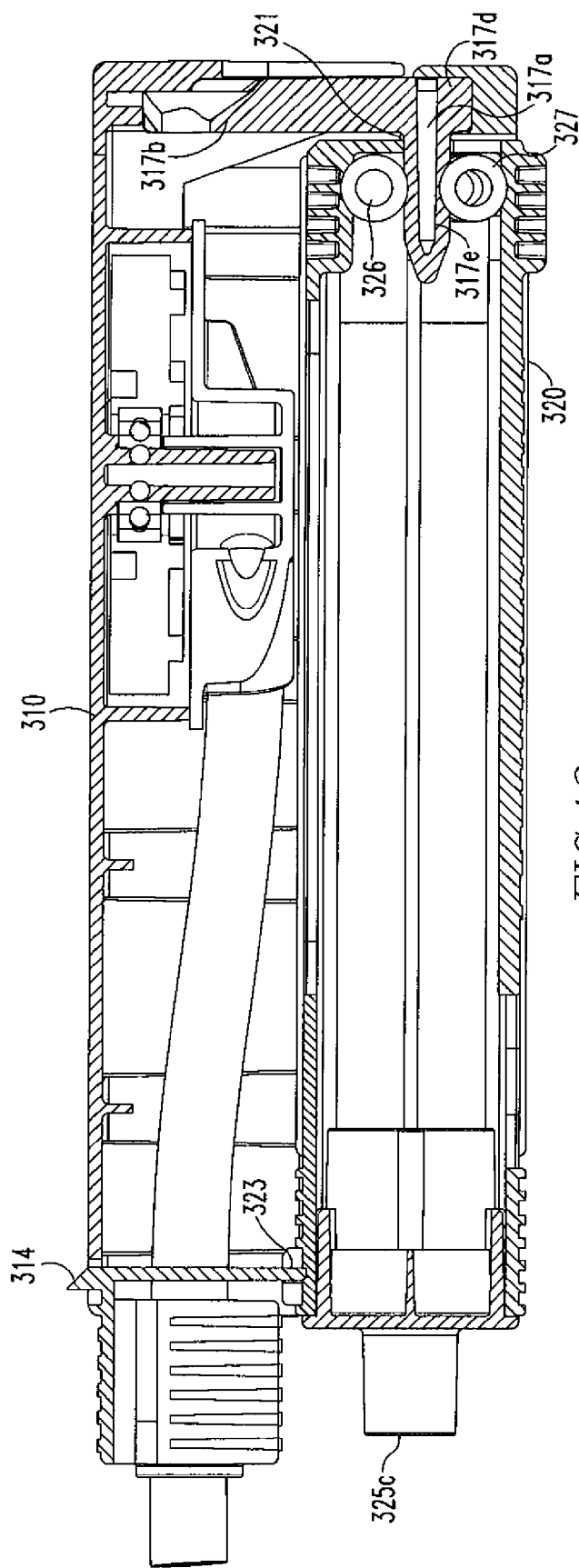
FIG. 12 is a cross-sectional view of the cartridge assembly of FIGS. 9 and 10.

The assembly slot 210 includes a latch slot 240 for receiving a latch 314 (FIG. 12) provided on the inflow cartridge 310, and a pair of contoured tracks 205 with which protrusions 315a-315c on the inflow cartridge 310 align as the cartridge assembly 300 is inserted into the slot 210. As mentioned above, control unit 200 includes a magnetic coupling system 230 for activating the centrifugal pump 312 of the inflow cartridge 310, e.g., through magnetic induction, non-contact activation of impellers (not shown) located within the pump 312. The coupling system 230 creates a magnetic field that operatively induces the impellers to move in response thereto, e.g., the impeller can include magnetic pickups that react to the magnetic field of the system 230. In addition, the magnets (not shown) associated with the system 230 and impeller can provide an attractive force that assists in locking or biasing the assembly within the assembly slot 210.

The pump control unit 200 includes the pair of pressure transducers 220a, 220b for measuring respective pressures P1, P2 across the flow restriction 370, a pinch valve 225 to control a flow of fluid returning from the joint cavity 10, and microswitches 260 for operatively engaging with a rear surface of the inflow cartridge 310 to detect cartridge type and to detect an operative connection with a properly inserted cartridge, all of which are more fully described in the '370 publication.

Figure 4:
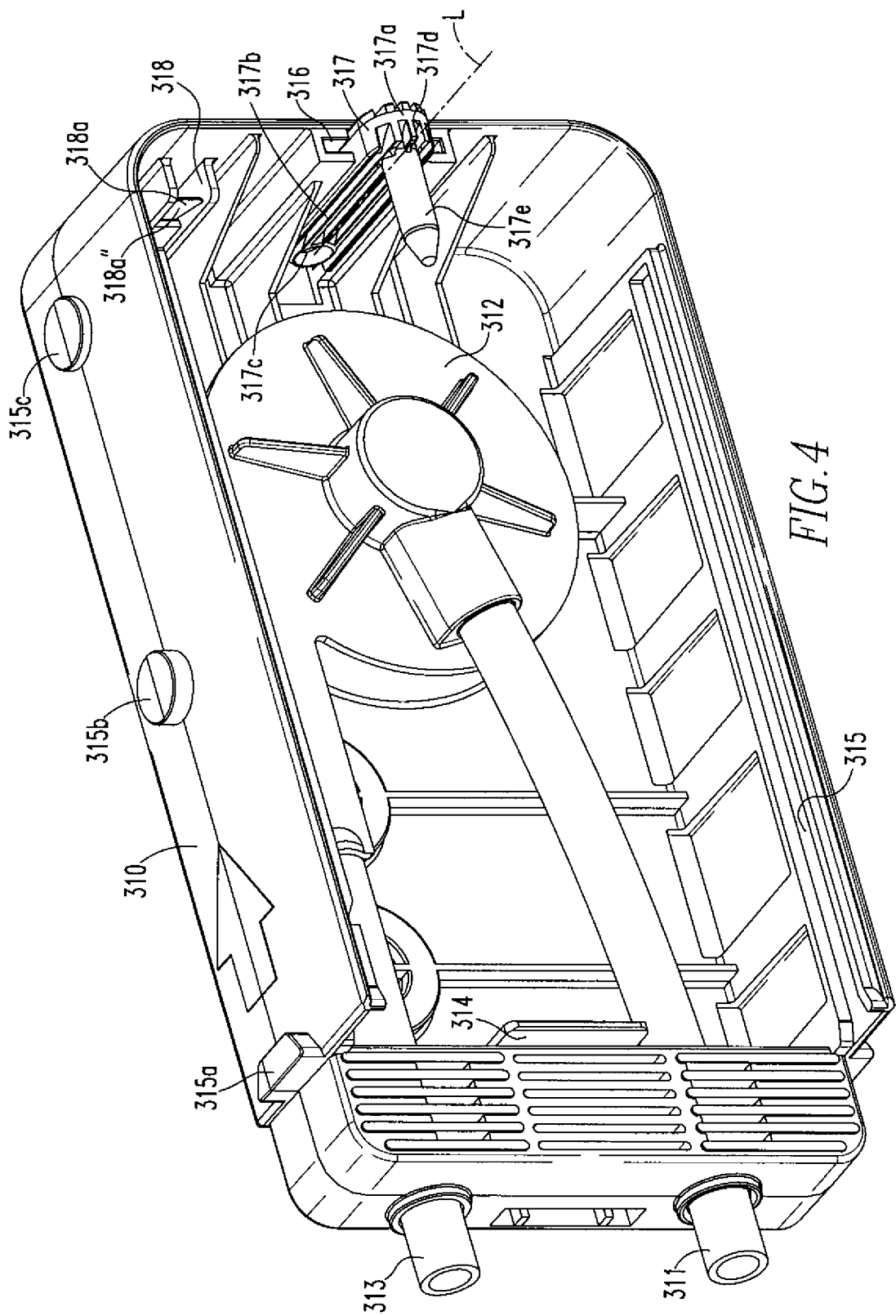
FIG. 4 shows a perspective view of the inflow cartridge of the fluid management system of FIG. 1.

FIG. 4 shows the inflow cartridge 310 of the present disclosure. As stated above, the cartridge 310 includes an inlet tubing connection 311, an outlet tubing connection 313, and a centrifugal pump 312. Fluid enters the cartridge 310 through the inlet tubing connection 311 and is received by the centrifugal pump 312. The fluid is then supplied to the joint cavity through the outlet tubing connection 313. The cartridge 310 also includes grooves 315 that are configured for lateral coupling of the outflow cartridge 320 to the inflow cartridge 310, which will be further described below. In addition, the latch 314, as described above, also serves to couple the outflow cartridge 320 to the inflow cartridge 310, as will be further described below.

The cartridge 310 includes an aperture 316 that houses an extender 317. The extender 317 includes a body 317a having a first end 317b that includes a hole 317c and a second end 317d that includes a hook 317e. The hook 317e extends perpendicular to a longitudinal axis L of the extender 317. As further described below and shown in FIG. 12, when the outflow cartridge 320 is coupled to the inflow cartridge 310, the hook 317e is disposed within an opening 321 on the outflow cartridge 320. When the cartridge 310 is located in the slot 210, the pinch valve 225 is housed within the hole 317c. As further described below, movement of the pinch valve 225 allows for control of fluid flow through the outflow cartridge 320.

Figure 10:
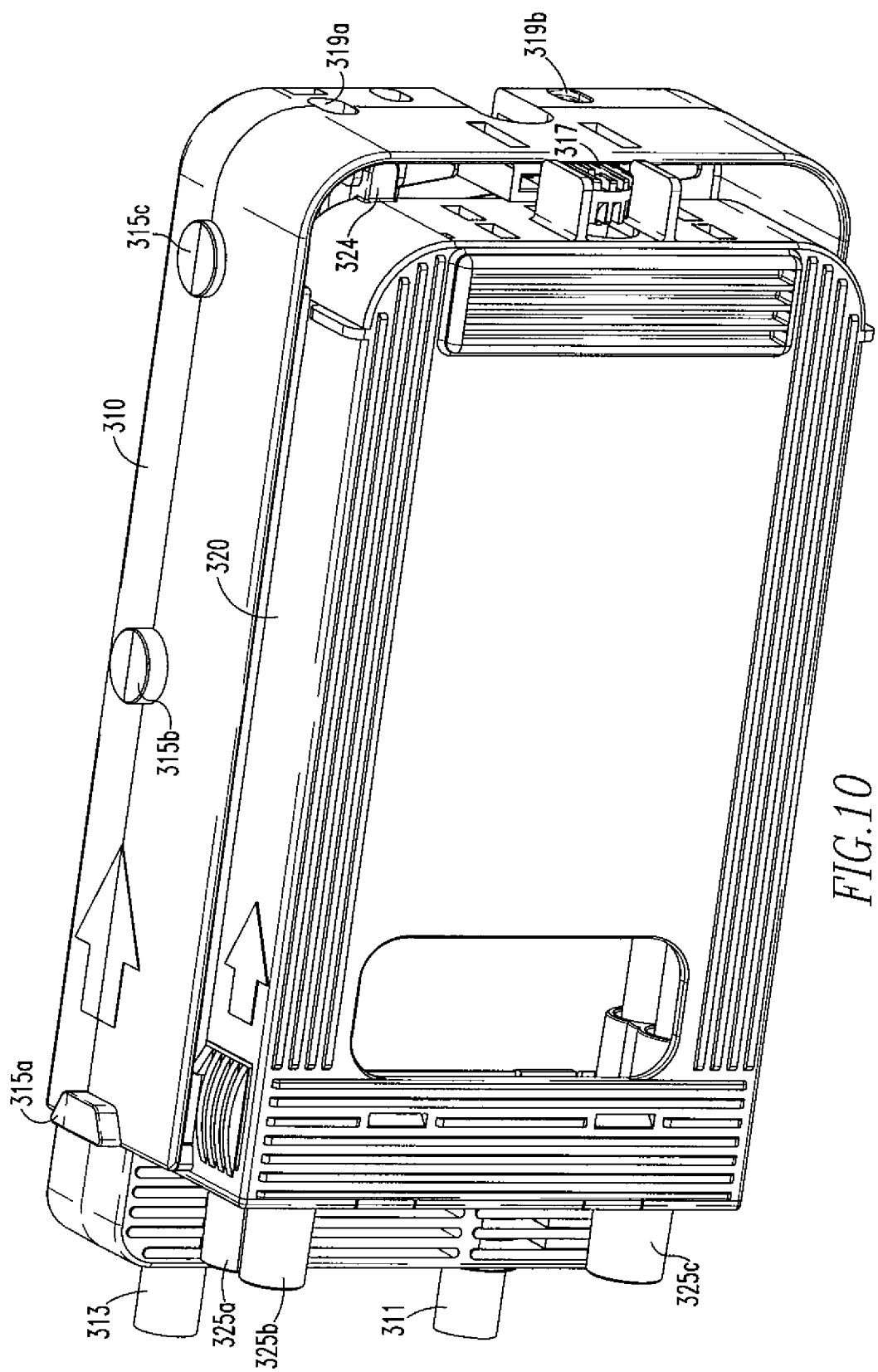

Furthermore, the inflow cartridge 310 includes a hollow 318, which houses an activator 318a. The activator 318a includes a first end (not shown) and a second end 318a". Openings (319a & 319b, FIG. 10), which exist on the cartridge 310, allow for housing of the microswitches 260. Opening 319a is located adjacent to the first end of the activator 318a. The microswitch 260 extends through the opening 319a and engages the first end of the activator 318a, thereby allowing the unit 200 to detect cartridge type and an operative connection with a properly inserted cartridge. As further described below, when the outflow cartridge 320 is coupled to the inflow cartridge 310, the outflow cartridge 320 engages the second end 318a" of the activator 318a to allow the unit 200 to detect a coupling of the outflow cartridge 320 to the inflow cartridge 310. The activator 318a includes spring steel, but may include other material.

Figure 5:
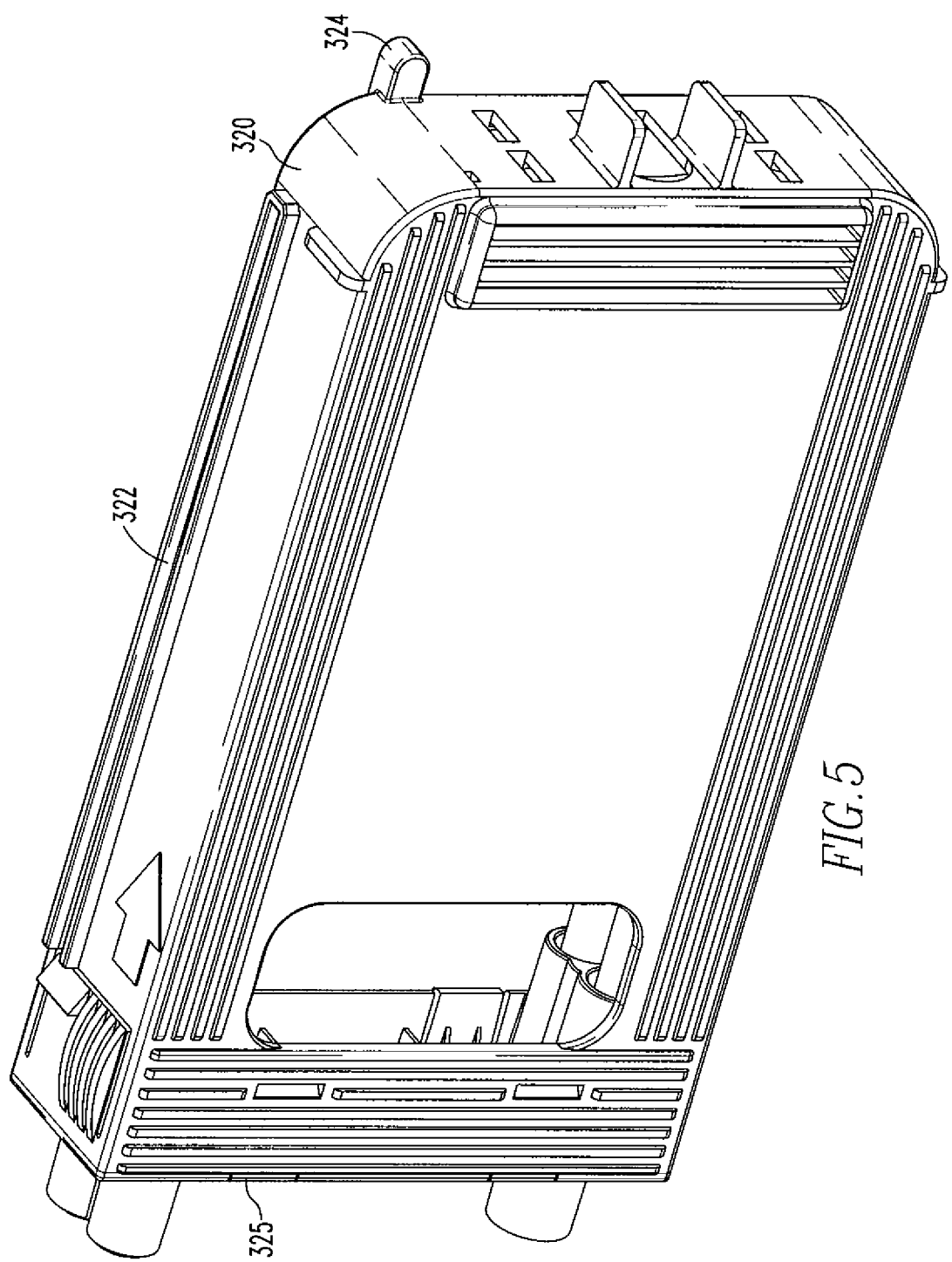
FIG. 5 shows a perspective view of the outflow cartridge of the fluid management system of FIG. 1.
Figure 6:
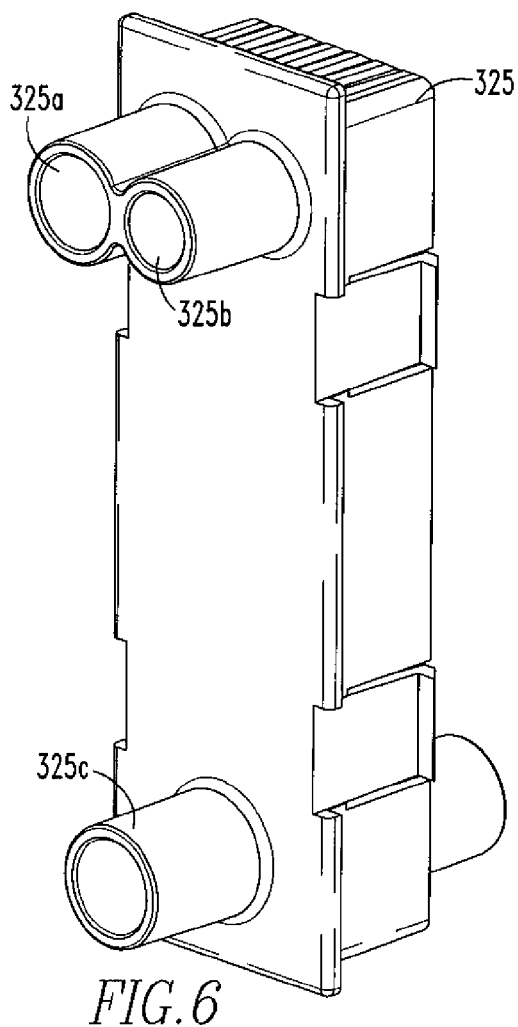
FIG. 6 is a perspective view of the nose piece of the outflow cartridge of FIG. 5.
Figure 7:
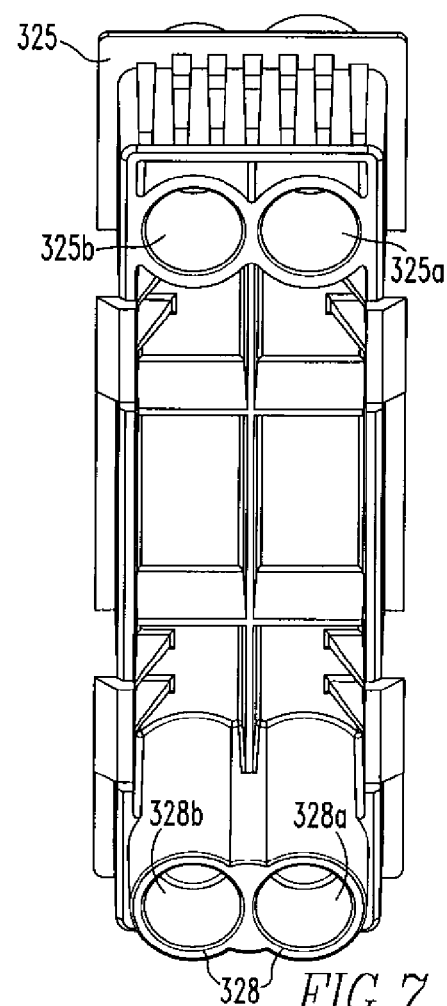
FIG. 7 is a rear view of the nose piece of FIG. 6.
Figure 8:
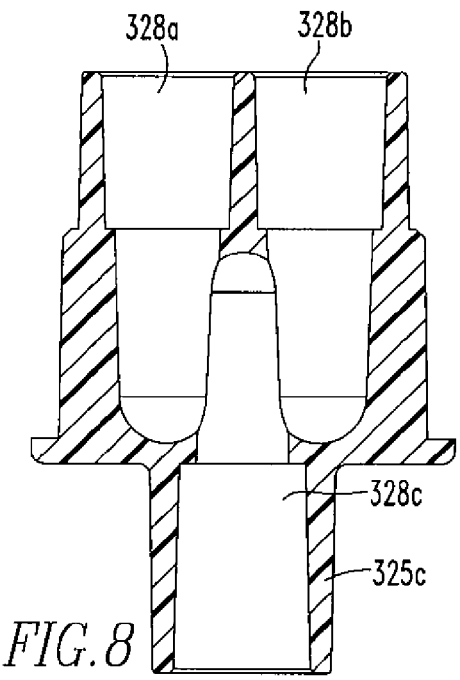
FIG. 8 is a cross-sectional view of the nose piece of FIG. 6.
Figure 9:
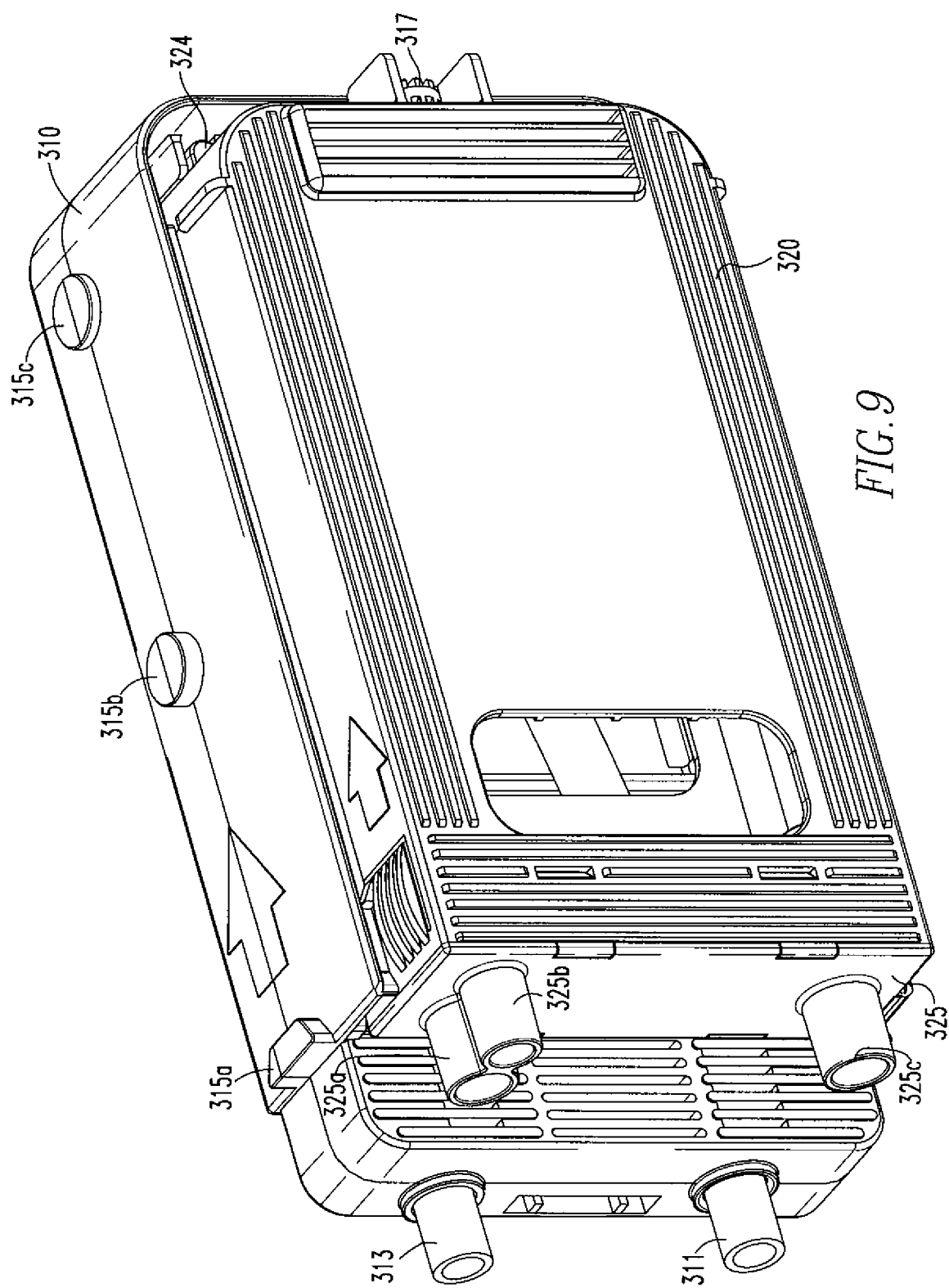
FIGS. 9 and 10 are perspective views of the cartridge assembly of the present disclosure.
Figure 11:
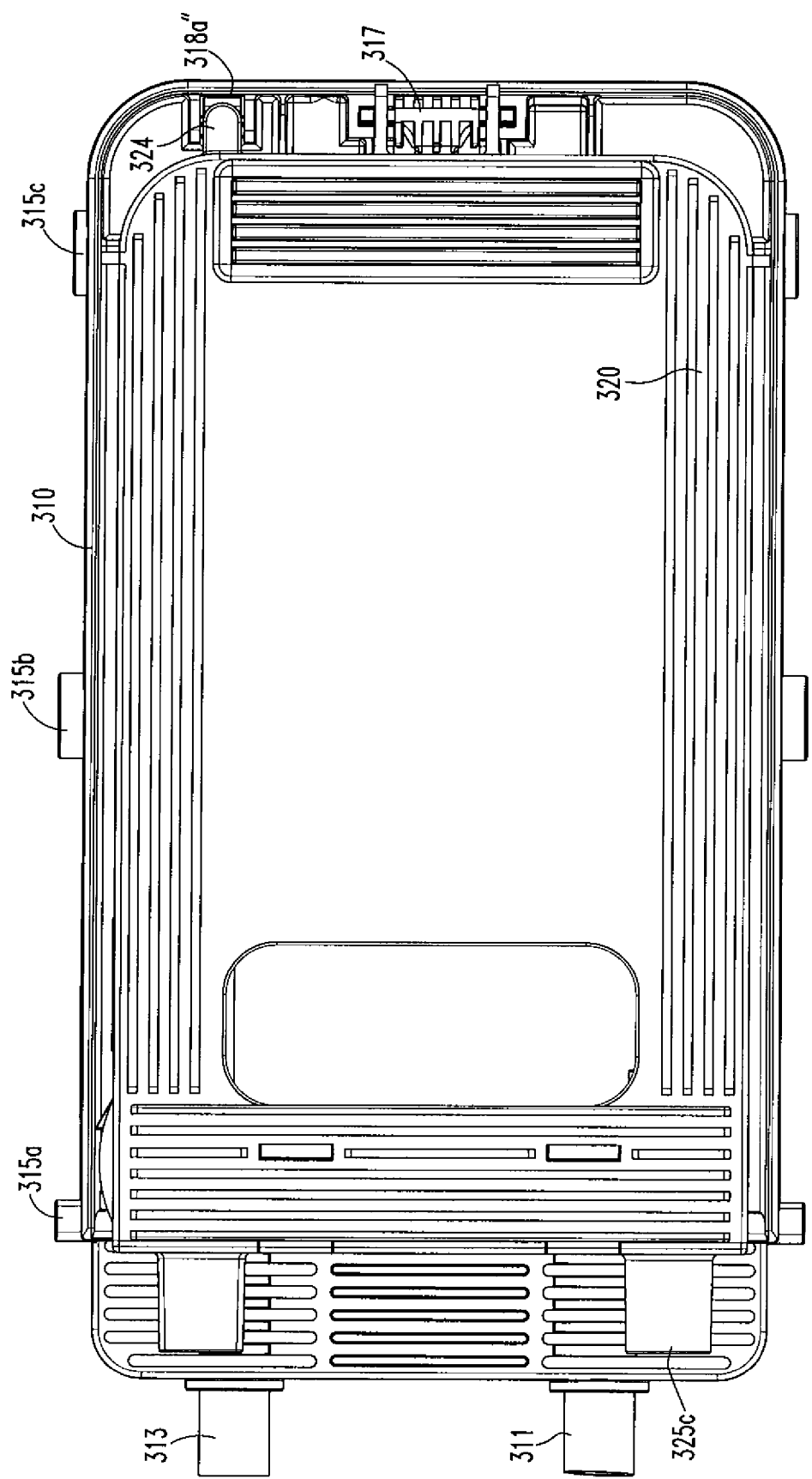
FIG. 11 is a side view of the cartridge assembly of FIGS. 9 and 10.

As shown in FIGS. 5 and 11, the outflow cartridge 320 includes rails 322 that allow for lateral coupling of the outflow cartridge 320 to the inflow cartridge 310 via disposal of the rails 322 in the grooves 315, as will be further described below. The outflow cartridge 320 is thereby slidably engaged with the inflow cartridge 310. The cartridge 320 also includes a slot (FIG. 12, 323), an opening 321, as mentioned above for receipt of the hook 317e, a tab 324, and a nose piece 325. As shown in FIGS. 6-8 and 12, the nose piece 325 includes a first tubing connector 325a, a second tubing connector 325b coupled to the first tubing connector 325a, and a third tubing connector 325c. Tubing 326,327 extending from the first tubing connector 325a and the second tubing connector 325b, respectively, are both coupled to the third tubing connector 325c via a connection assembly 328, as shown in FIG. 8. The assembly 328 includes a first connection port 328a for disposal of tubing 326 and a second disposal port 328b for disposal of tubing 327. Both ports 328a,328b are coupled to a third connection port 328c, which is coupled to the third tubing connector 325c. As will be further described below, fluid flowing through tubings 326,327 will exit the outflow cartridge 320 via only the third tubing connector 325c. The nose piece 325 is snap mounted to the outflow cartridge 320, but may be coupled via another method known to one of skill in the art.

FIGS. 9-12 show that upon coupling of the outflow cartridge 320 to the inflow cartridge 310, the latch 314 extends into the slot 323 to further couple the cartridges 310,320. In addition, FIG. 12 further shows that hook 317e extends through the opening 321 and is located between the tubings 326,327. As further described below, during use, the pinch valve 225 oscillates, e.g. in a reciprocating or lateral motion, to apply and release a restricting action to the tubings 326,327, thereby controlling the flow of waste fluid leaving a joint cavity. In addition, as shown in FIG. 11, upon coupling of the cartridges 310,320, the tab 324 engages the second end 318a" of the activator 318a, thereby allowing the unit 200 to detect a coupling of the outflow cartridge 320 to the inflow cartridge 310.

Figure 13:
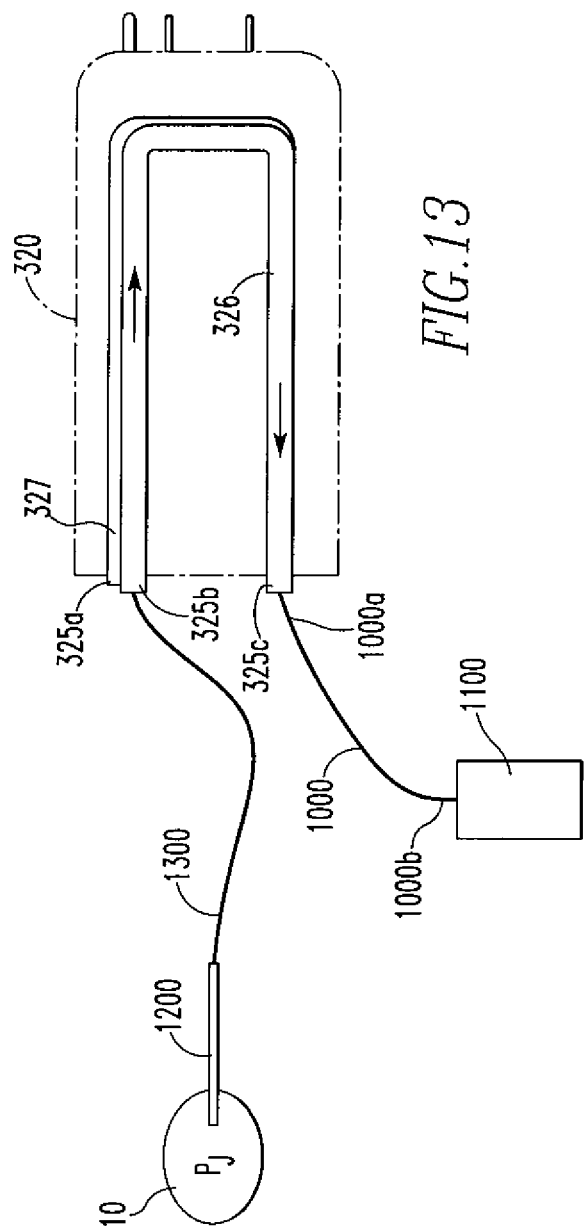
FIG. 13 is another schematic of the fluid management system of FIG. 1 in use during an endoscopic surgical procedure.

As shown in FIG. 13, during use tubing 1000 is coupled to the third tubing connector 325c at one end 1000a of the tubing 1000 and the second end 1000b of the tubing 1000, which is located below the cartridge 320, is disposed within a waste collection bag or container 1100. In this manner, the flow of waste fluid from the joint cavity 10 is gravity controlled. Alternatively, the second end 1000b of the tubing 1000 is coupled to a vacuum and the flow of waste fluid from the joint cavity 10 is vacuum controlled. The waste fluid from the joint cavity 10 enters the cartridge 320 via cannulas 1200 and tubing 1300 that are coupled to the first and second tubing connectors 325a,325b. The waste fluid is moved through the cartridge 320 via tubings 326,327. As mentioned above, the pinch valve (not shown) oscillates to apply and release a restricting action to the tubings (not shown), thereby controlling the flow of waste fluid leaving the joint cavity. The cyclical action of the restricting force to the tubings 326,327 substantially reduces clogging and buildup of fluid and debris evacuated from the joint cavity. In addition, the pinch valve (not shown) permits the controlled reduction of fluid flow from the joint cavity.

The cartridge assembly 300 may include mechanical means of coupling the inflow cartridge to the outflow cartridge, other than the rails 322 and grooves 315, such as a snap-in, twist-on, or other mechanical means.

Figure 14:
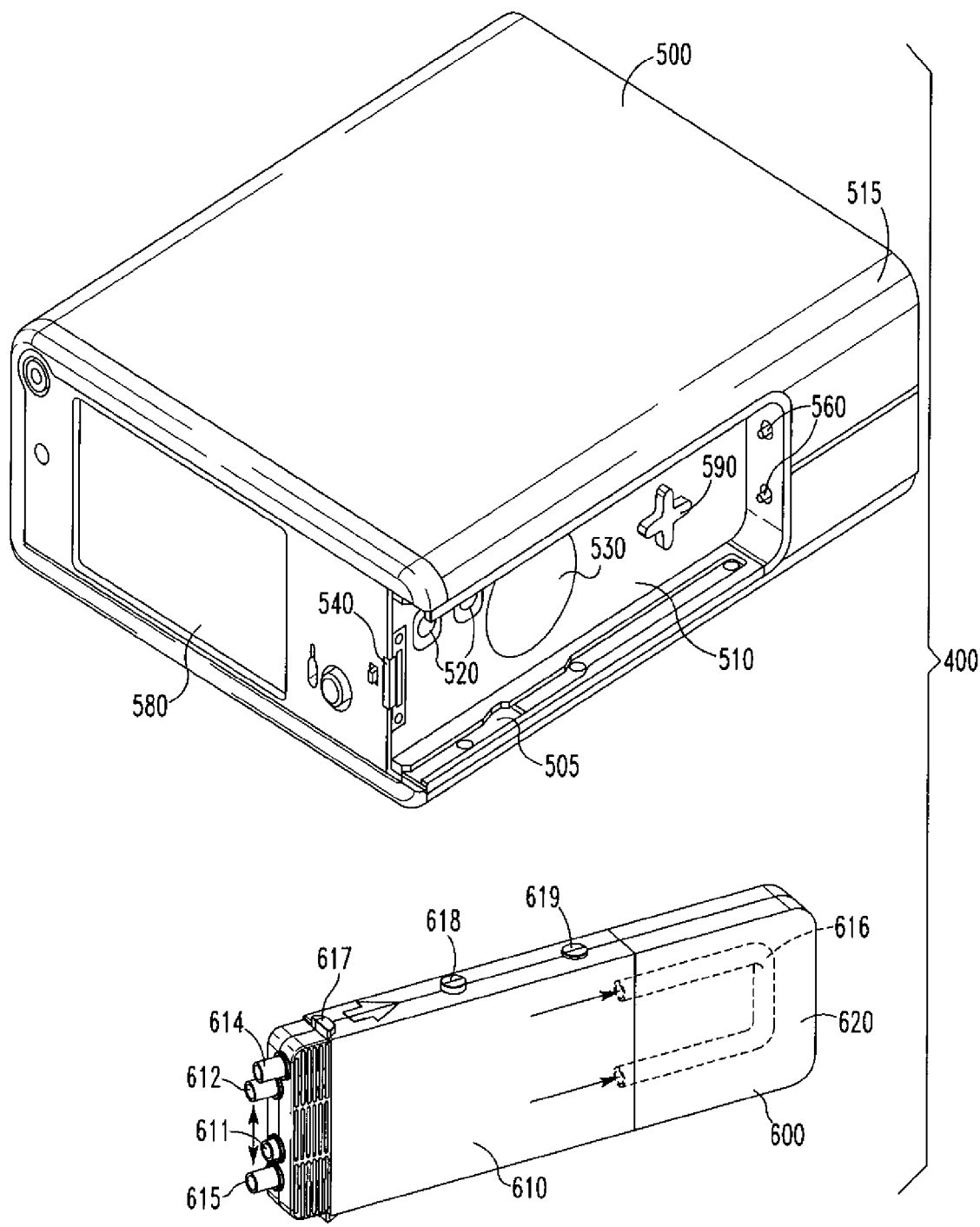
FIG. 14 illustrates components of a second embodiment of the fluid management system of the present disclosure.

FIG. 14 shows a second embodiment of the fluid management system 400 of the present disclosure. The system 400 includes a pump control unit 500 and a cartridge assembly 600 coupled to the pump control unit 500. Similar to pump control unit 200, the pump control unit 500 includes a housing 515, a rectangular-shaped slot 510 for operatively receiving the cartridge assembly 600, a display 580, pressure transducers 520, a latch slot 540, a magnetic coupling system 530, and microswitches 560. However, the unit 500 does not include a pinch valve for controlling the flow of waste fluid returning from the joint cavity. Rather, the unit 500 includes a rotor 590 that acts to drive waste fluid, via positive displacement, from the cavity through the outflow cartridge 620 and into a waste container, as will be further described below.

The cartridge assembly 600 includes an inflow cartridge 610 and an outflow cartridge 620 coupled to and located proximal to the inflow cartridge 610. For the purposes of this disclosure, the inflow and outflow cartridges 610 are coupled via coupling methods including, but not limited to, rails that allow for the cartridges 610,620 to be slidably coupled, hinges that allow for hinged coupling, snap-on features that allow for the cartridges 610,620 to be snapped on to each other, and latches that allow for the cartridges 610,620 to be latched to one another. Similar to the inflow cartridge 510, the inflow cartridge 610 includes an inlet tubing connection 611, an outlet tubing connection 612, and a centrifugal pump (not shown). Fluid enters the cartridge 610 through the inlet tubing connection 611 and is received by the centrifugal pump (not shown). The fluid is then supplied to the joint cavity through the outlet tubing connection 612. The inflow cartridge 610 also includes an inlet tubing connection 614, an outlet tubing connection 615, and a waste fluid return line 616 coupled to and located between the connections 614,615. The cartridge assembly 600 is coupled to the unit 500 by sliding the assembly 600 into the slot 510, such that a latch (not shown), similar to latch 314, on the inflow cartridge 610 is received in the latch slot 540, the protrusions 617-619 on the inflow cartridge 610 align with the tracks 505, and the waste fluid return line 616 is disposed around the rotor 590. As the rotor 590 rotates, it engages the waste fluid return line 616, thereby creating positive displacement, as mentioned above, of the waste fluid from the surgical site. The waste fluid flows through a tubing (not shown) located at the surgical site, through the inflow and outflow cartridges 610,620 via the inlet tubing connection 614, outlet tubing connection 615, and waste fluid return line 616, and into a waste container (not shown) via a tubing (not shown) coupled to the outlet tubing connection 615.

Figure 15:
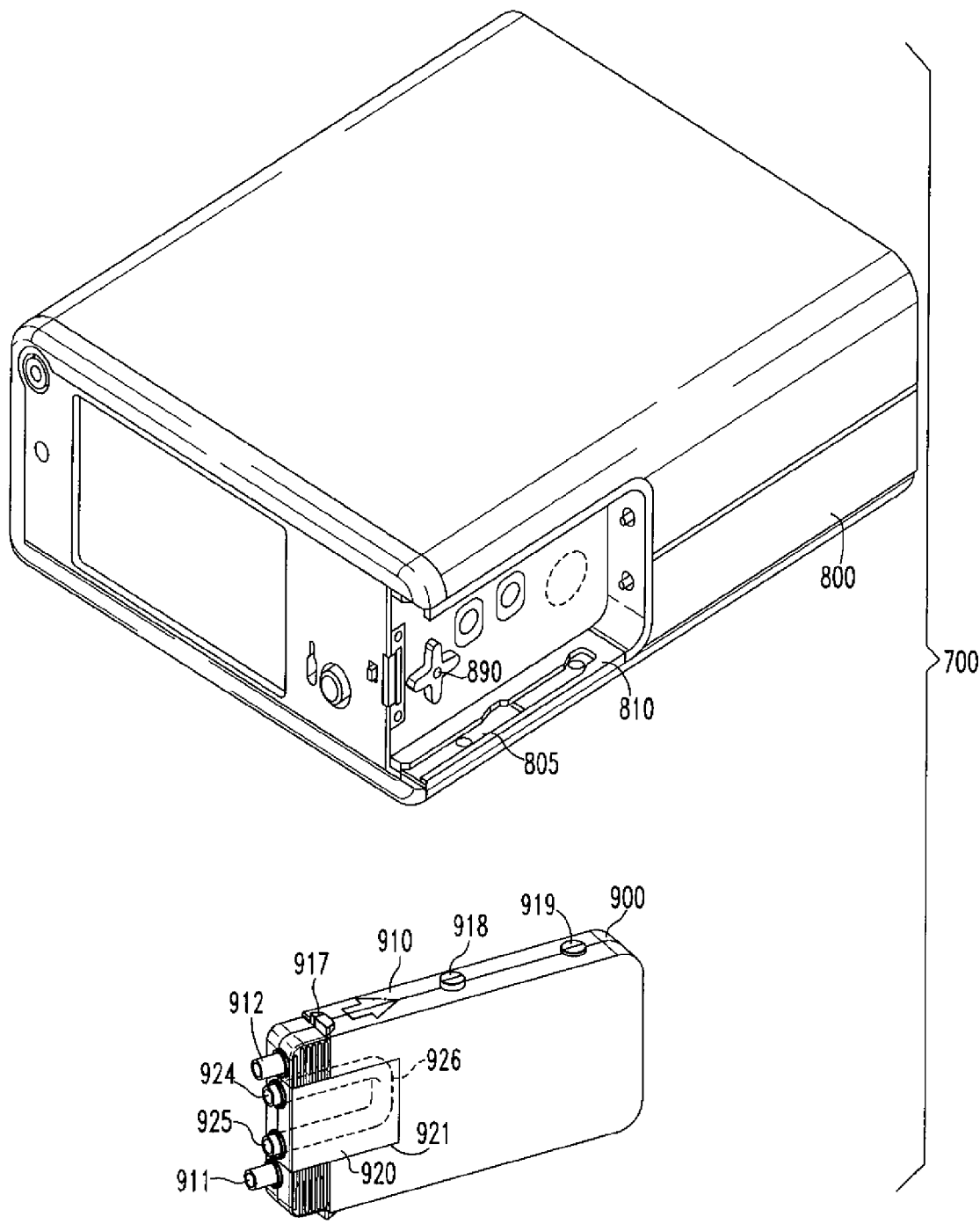
FIG. 15 illustrates components of a third embodiment of the fluid management system of the present disclosure.

FIG. 15 shows a third embodiment of the fluid management system 700 of the present disclosure. Similar to pump control unit 500, pump control unit 800 includes a rotor 890 that acts to drive waste fluid, via positive displacement, from the joint cavity through the outflow cartridge 920 and into a waste container, as will be further described below.

The cartridge assembly 900 includes an inflow cartridge 910 and an outflow cartridge 920 coupled to and located within a pocket 921 on the inflow cartridge 910. For the purposes of this disclosure, the cartridges 910,920 may be coupled via the coupling methods listed above for coupling of cartridges 610,620 or other methods known to one of skill in the art. Similar to the inflow cartridge 610, the inflow cartridge 910 includes an inlet tubing connection 911, an outlet tubing connection 912, and a centrifugal pump (not shown). Fluid enters the cartridge 910 through the inlet tubing connection 911 and is received by the centrifugal pump (not shown). The fluid is then supplied to the joint cavity through the outlet tubing connection 912. The outflow cartridge 920 includes an inlet tubing connection 924, an outlet tubing connection 925, and a waste fluid return line 926 coupled to and located between the connections 924, 925. The cartridge assembly 900 is coupled to the unit 800 by sliding the assembly 900 into the slot 810, such that the protrusions 917-919 on the inflow cartridge 910 align with the tracks 805, and the waste fluid return line 926 is disposed around the rotor 890.

As the rotor 890 rotates, it engages the waste fluid return line 926, thereby creating positive displacement, as mentioned above, of the waste fluid from the surgical site. The waste fluid flows through a tubing (not shown) located at the surgical site, through the outflow cartridge 920 via the inlet tubing connection 924, outlet tubing connection 925, and waste fluid return line 926, and into a waste container (not shown) via a tubing (not shown) coupled to the outlet tubing connection 925.

The cartridge assemblies and their components are made from metal and non-metal material, such as plastic, via methods including, but not limited to, injection molding, reaction injection molding (RIM), resin casting, machining, and extrusion. In addition, the tubings coupled to the inlet and outlet connectors and the tubings located within the inlet and outlet cartridges are made from medical grade material, including, but not limited to, clear, soft, and/or relatively rigid poly-vinyl chloride (PVC) tubing material.

The present disclosure provides disposable, sterile, cartridge assemblies including one inflow and one outflow component, whereby the outflow component can be replaced independently and whereby the inflow component can remain in place to provide continued use. Versatility and flexibility is enhanced due to the possibility that the outflow cartridge may be independently added to and removed from the inflow cartridge, if needed. The assemblies also provide increased conservation of surgical irrigation solution usage and cost effectiveness when compared to single use cartridges that are disposed of after each use. In addition, the assemblies provide ease of use when compared to pump systems using completely separate inflow and outflow tubing systems.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A surgical fluid management system comprising:
a pump control unit that includes a pinch valve, and
a cartridge assembly coupled to the pump control unit, the assembly comprising an inflow cartridge and an outflow cartridge removably and directly coupled to the inflow cartridge;
an extender coupled to the inflow cartridge, the extender including a first end having a hole and a second end having a hook, the hook running perpendicular to the longitudinal axis of the extender;
said pinch valve is disposed within the hole and the hook is disposed within an opening on the outflow cartridge;
said inflow cartridge includes mechanisms to supply surgical fluid to a surgical site but does not receive surgical fluid from the surgical site, and the outflow cartridge includes mechanisms to receive and control flow of surgical fluid from the surgical site by restricting flow through the outflow cartridge but does not pump surgical fluid relative to the surgical site.

2. The fluid management system of claim 1 wherein the outflow cartridge includes a nose piece, the nose piece including a first tubing connector, a second tubing connector coupled to the first tubing connector, and a third tubing connector.

3. The fluid management system of claim 2 wherein tubing extending from both the first tubing connector and the second tubing connector are coupled to the third tubing connector, the hook located between the tubing such that movement of the pinch valve engages the pinch valve with either the tubing extending from the first tubing connector or the tubing extending from the second tubing connector.

4. The fluid management system of claim 2 wherein engagement of the pinch valve with either the tubing extending from the first tubing connector or the tubing extending from the second tubing connector controls fluid flow through the outflow cartridge.

5. The fluid management system of claim 1 wherein the pump control unit includes a cartridge recognition switch, the switch disposed within an opening in the inflow cartridge.

6. The fluid management system of claim 5 wherein the inflow cartridge includes an activator, the activator having a first end engaged with the switch and a second end.

7. The fluid management system of claim 1 wherein the pump control unit includes a magnetic coupling system.

8. The fluid management system of claim 7 wherein the inflow cartridge includes a centrifugal pump, the magnetic coupling system and the centrifugal pump acting together to drive fluid through the inflow cartridge.

9. The fluid management system of claim 1 wherein a vacuum source is coupled to the outflow cartridge.

10. The fluid management system of claim 1 wherein the pump control unit includes a rotor.

11. The fluid management system of claim 10 wherein tubing of the outflow cartridge is coupled to the rotor, the rotor acting to drive fluid through the outflow tubing.

12. The cartridge assembly of claim 1 wherein the inflow cartridge includes a pocket, the outflow cartridge located within the pocket.

13. A surgical fluid management system comprising:
   a cartridge assembly, the assembly comprising an inflow cartridge and an outflow cartridge removably and directly coupled to the inflow cartridge;
   a pump control unit coupled to the cartridge assembly, the pump control unit includes a cartridge recognition switch, the cartridge recognition switch disposed within an opening in the inflow cartridge;
   the inflow cartridge includes an activator, the activator having a first end engaged with the cartridge recognition switch and a second end;
   the outflow cartridge includes a tab, the tab engaged with the second end of the activator;
   wherein the inflow cartridge includes mechanisms to supply surgical fluid to a surgical site but does not receive surgical fluid from the surgical site, and the outflow cartridge site by restricting flow through the outflow cartridge but does not pump surgical fluid relative to the surgical site.

14. The fluid management system of claim 13 wherein engagement of the tab with the second end of the activator provides recognition of connection and removal of the outflow cartridge relative to the inflow cartridge.

15. The fluid management system of claim 13 wherein the pump control unit includes a pinch valve.

16. The fluid management system of claim 15 wherein an extender is coupled to the inflow cartridge, the extender including a first end having a hole and a second end having a hook, the hook running perpendicular to a longitudinal axis of the extender.

* * * * *